US009358573B2

United States Patent
Volny et al.

(10) Patent No.: US 9,358,573 B2
(45) Date of Patent: Jun. 7, 2016

(54) METHOD OF SURFACE MODIFICATION FOR ANALYZING PHOSPHORYLATED PEPTIDES

(75) Inventors: Michael Volny, Prague (CZ); Petr Novak, Dolni Brezany (CZ); Vladimir Havlicek, Prague (CZ); Petr Pompach, Mratin (CZ)

(73) Assignee: INSTITUTE OF MICROBIOLOGY AS CR, V.V.I., Prague (CZ)

( * ) Notice: Subject to any disclaimer, the term of this patent is extended or adjusted under 35 U.S.C. 154(b) by 161 days.

(21) Appl. No.: 13/993,912

(22) PCT Filed: Dec. 14, 2011

(86) PCT No.: PCT/CZ2011/000118
§ 371 (c)(1), (2), (4) Date: Jun. 13, 2013

(87) PCT Pub. No.: WO2012/079549
PCT Pub. Date: Jun. 21, 2012

(65) Prior Publication Data
US 2013/0260050 A1    Oct. 3, 2013

(30) Foreign Application Priority Data
Dec. 14, 2010    (CZ) .............. PV 2010-929

(51) Int. Cl.
*B05D 1/06* (2006.01)
*B05D 1/04* (2006.01)
*C07K 1/22* (2006.01)
*H01J 49/16* (2006.01)

(52) U.S. Cl.
CPC . *B05D 1/045* (2013.01); *C07K 1/22* (2013.01); *H01J 49/164* (2013.01)

(58) Field of Classification Search
CPC .......... B05D 1/045; C07K 1/22; H01J 49/164
USPC ................................... 427/458–486
See application file for complete search history.

(56) References Cited

U.S. PATENT DOCUMENTS

| 7,214,353 B2 | 5/2007 | Feuer et al. |
| 7,381,373 B2* | 6/2008 | Blake et al. ............ 250/284 |
| 2004/0119010 A1 | 6/2004 | Perryman et al. |
| 2006/0145089 A1 | 7/2006 | Cristoni et al. |
| 2007/0113530 A1* | 5/2007 | Morozov et al. ............. 55/527 |
| 2009/0152371 A1* | 6/2009 | Stark et al. ............. 239/3 |

FOREIGN PATENT DOCUMENTS

| CN | 101825615 | 9/2010 |
| EP | 1 612 550 | 1/2006 |
| WO | WO 2004034011 | 4/2004 |

* cited by examiner

*Primary Examiner* — Alexander Weddle
(74) *Attorney, Agent, or Firm* — Notaro, Michalos & Zaccaria P.C.

(57) ABSTRACT

A method of surface modification for analyzing of phosphorylated peptides. The surface of solid substrates is modified for efficient phosphorylated peptide preconcentration from complex peptide mixtures prior to detection based on desorption/ionization mass spectrometry. The method of surface functionalization is introduced by ambient ion landing. The approach is based on electronebulization, differently said electrospray, of solutions of organometallic compounds related to elements of 4B class of periodic table of elements, especially to zirconium, hafnium and titanium. The generated charged electrospray is dried on the fly by passing the heated compartment and focused to a surface for modification forming a stable oxide layer there. The surface modified this way has been used for phosphopeptide enrichment from peptide mixtures prior to desorption/ionization mass spectrometry.

5 Claims, 4 Drawing Sheets

A                               B                               C

Figure 5

Figure 1:
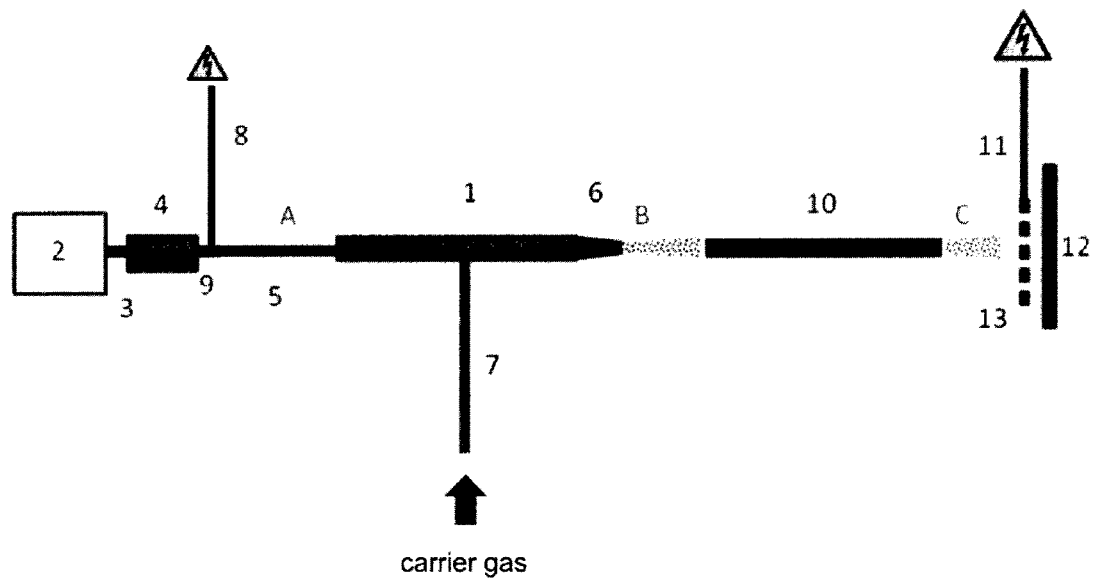

| Peak No. | m/z (charge) | peptide | No. of phosphorylations | casein | 2 | 3 | 4 | 5 | 6 |
|---|---|---|---|---|---|---|---|---|---|
| 1 | 1031.42440 (2+) | FQ-pS-EEQQQTEDELQDK | 1 | beta | + | - | - | - | - |
| 2 | 1561.63686 (2+) | RELEELNVPGEIVE-pS-L-pS-pS-pS-EESITR | 4 | beta | + | - | - | - | - |
| 9 | 2061.82930 (1+) | FQ-pS-EEQQQTEDELQDK | 1 | beta | + | + | + | + | + |
| 10 | 2556.08588 (1+) | FQ-pS-EEQQQTEDELQDKIHPF | 1 | beta | + | + | + | - | + |
| 17 | 2966.19345 (1+) | ELEELNVPGEIVE-pS-L-pS-pS-pS-EESITR | 4 | beta | + | - | - | + | - |
| 18 | 2962.37302 (1+) | RELEELNVPGEIVE-pS-L-pS-SSEESITR | 2 | beta | - | - | - | - | - |
| 19 | 3042.27711 (1+) | RELEELNVPGEIVE-pS-L-pS-pS-SEESITR | 3 | beta | - | - | - | - | - |
| 20 | 3122.26464 (1+) | RELEELNVPGEIVE-pS-L-pS-pS-pS-EESITR | 4 | beta | + | + | + | + | + |

Figure 6

| Peak No. | m/z (charge) | peptide | No. of phosphorylations | casein | 1 | 2 | 4 | 5 | 6 |
|---|---|---|---|---|---|---|---|---|---|
| 3 | 1660.79372 (1+) | VPQLEIVPN-pS-AEER | 1 | alpha S1 | + | + | + | + | + |
| 4 | 1832.85326 (1+) | YLGEYLIVPNSAEER | 1 | alpha S1 | - | - | + | + | - |
| 5 | 1863.71919 (1+) | DIG-pS-ESTEDQA-oxM-EDIK | 1 | alpha S1 | - | - | - | - | - |
| 6 | 1927.69375 (1+) | DIG-pS-E-pS-TEDQAMEDIK | 2 | alpha S1 | - | - | - | + | + |
| 7 | 1943.68659 (1+) | DIG-pS-E-pS-TEDQA-oxM-EDIK | 2 | alpha S1 | - | - | + | - | - |
| 8 | 1951.95287 (1+) | YKVPQLEIVPN-pS-AEER | 1 | alpha S1 | + | + | + | + | + |
| 11 | 2559.94371 (1+) | Q(deamido)-oxM-EAE-pS-I-pS-pS-SEEIVPNSVEQK | 3 | alpha S1 | - | - | - | - | - |
| 12 | 2576.99571 (1+) | Q-oxM-EAE-pS-I-pS-pS-SEEIVPNSVEQK | 3 | alpha S1 | - | - | - | - | - |
| 13 | 2639.93462 (1+) | Q(deamido)-oxM-EAE-pS-I-pS-pS-pS-EEIVPNSVEQK | 4 | alpha S1 | - | - | - | - | - |
| 14 | 2656.95603 (1+) | Q-oxM-EAE-pS-I-pS-pS-pS-EEIVPNSVEQK | 4 | alpha S1 | - | - | - | - | - |
| 15 | 2719.90729 (1+) | Q(deamido)-oxM-EAE-pS-I-pS-pS-pS-EEIVPN-pS-VEQK | 5 | alpha S1 | - | - | - | - | - |
| 16 | 2736.92778 (1+) | Q-oxM-EAE-pS-I-pS-pS-pS-EEIVPN-pS-VEQK | 5 | alpha S1 | - | - | - | - | - |

METHOD OF SURFACE MODIFICATION FOR ANALYZING PHOSPHORYLATED PEPTIDES

TECHNICAL FIELD

Phosphoproteomics; surfaces modified for desorption/ionization mass spectrometry Modification of solid substrates for efficient surface preconcentration of phosphopeptides from complex peptide mixtures prior to detection based on desorption/ionization mass spectrometry

BACKGROUND ART

Chemical changes of cellular proteins, also called post-translational modifications, reflect important and complex biochemical processes directly related to cell biological conditions. Hence, these posttranslational modifications are linked to multiple disease states including cancer and their structural determination represents a prerequisite for definition and development of new targeted therapies. Protein phosphorylation represents one of the most important signaling modifications mandatory for regulation of most of cellular processes. Standard bottom-up proteomic approaches (Aebersold, 2001) based on high performance liquid chromatography/tandem mass spectrometry cannot easily discriminate between non-phosphorylated and phosphorylated peptides due to the effect of negatively-charged phospho-group deteriorating the signal in positive ion electrospray mass spectra, so fractionation and further identification steps are needed. There have been reported chemical and affinity approaches being used for discrimination of phosphopeptides from regular peptides (Bodenmiller, 2007). Chemical methods were based in beta-elimination of a phosphate group. The double bond formed this way then reacted with various nucleophilic agents carrying some functional group which subsequently was used for selective isolation. Phosphoramidate chemistry served as one important example (Zhou, 2001). Affinity techniques have been based on phosphopeptide separation from a complex mixture by affinity interaction with solid substrate. Immobilized metal affinity chromatography (IMAC) or the application of metal oxides, e.g. $TiO_2$, $ZrO_2$, $Al_2O_3$ have been usually combined either on-line or off-line with some chromatographic separation. Electrospray (ESI) and/or matrix-assisted laser desorption ionization (MALDI) were common ionization techniques. Most challenging tasks remained the lack of automation and problems associated with small sample volume operations. Therefore, we started with phosphopeptide enrichment directly on MALDI target surface on which the desorption and ionization processes take place. In these experiments the surface, at which the phosphopeptides are going to be analyzed, is modified by application of affinity substrate, which more readily binds phosphopeptides compared to non-phosphorylated compounds. Upon selective elution of the non-phosphorylated material, phosphorylated peptides are determined by standard MALDI mass spectrometry experiment. This approach is easier compared to electrospray ionization (both in on- and offline setup) and lower detection limit can be achieved. The problem remains the discovery of a suitable way of surface modification of a MALDI target. Most common modification materials are titanium and zirconium oxides. The active surface has been prepared in multiple ways mostly suffering from complications both in sample preparation and phosphopeptide analysis. Blacken (Blacken 2007, 2009) employed a reactive landing procedure, which was ultra-low pressure experiment based on surface bombardment by desolvated ions or their clusters prepared from 4B atom propoxides (Løver, 1997). The charged clusters of stable isotopes prepared this way had to be accelerated by external electric field (up to 15 kV) to hypertermal energies being thousand times higher than normal internal laboratory temperature (Blacken 2007, 2009). Kinetic energy of these projectiles was converted into internal energy during the surface-induced collision process and surface modification. Although this technique gave quality and mechanically stable surfaces, the process was long lasting (several hours) and evacuated device was costly. Upon the introduction of a surface into the instrument, high vacuum had to be reached first and then a 3-hour propoxide deposition could start. The process was not high-throughput and price of surface modification carried this way was high. The second reported process was based on $TiO_2$-assisted pulsed laser deposition (Torta, 2009). This latter approach provided low-quality surfaces and was also costly. Standard "wet" electrospray deposition of zirconium oxide on a heated surface represented another alternative. Elevated surface temperature, however, caused the fragile and chapped layer formation (Blacken 2009 and our observations). Titanium oxide also could be directly deposited (Niklew, 2010). This procedure was very difficult as $TiO_2$ is water insoluble and in fact a suspension had to be directly sprayed onto a surface causing clogging the spray needle and ion current instability. Other technical variants are cited in FIGS. 5 and 6 and declare that our approach reported in this application gives the best results ever reported.

LITERATURE

Aebersold R, Goodlett D R: CHEMICAL REVIEWS (2001) 101, 2, 269-295.

Blacken, G R; Volny, M; Diener, M, et al.: JOURNAL OF THE AMERICAN SOCIETY FOR MASS SPECTROMETRY (2009) 20, 6, 915-926.

Blacken, G R; Volny, M; Vaisar, T, et al.: ANALYTICAL CHEMISTRY (2007) 79, 14, 5449-5456.

Bodenmiller B, Mueller L N, Mueller M, Domon B, Aebersold R: NATURE METHODS (2007) 4, 3, 231-237.

Lover T, Henderson W, Bowmaker G A, Seakins J M, Cooney R P: JOURNAL OF MATERIALS CHEMISTRY (1997) 7, 8, 1553-1558.

Niklew M L Analytical Chemistry 2010, 82, 1047-1053

Torta F, Fusi, Casari C S, Bottani C E, Bachi A: JOURNAL OF PROTEOME RESEARCH (2009) 8, 4, 1932-1942.

Zhou H L, Watts J D, Aebersold R: NATURE BIOTECHNOLOGY (2001) 19, 4, 375-378.

DISCLOSURE OF THE INVENTION

We report on a new method of surface modification needed for efficient separation of phosphopeptides from complex mixtures, which is easy and provides stable and high-quality surfaces. Surface modification was achieved by pneumatically-assisted electrospray of non-aqueous alcoholic solutions of titanium, zirconium and hafnium alkoxides at atmospheric pressure. Any inert gas or oxygen can be used as carrier gas. Aerosol formed by spraying was nebulized by carrier gas and dried in a heated region. Charged aerosol particle was driven by electrostatic forces defined and targeted towards the surface to be modified. Surface functionalization was achieved by stable sticking of titanium, zirconium or hafnium oxides. Any material with maximal resistivity $10^{20}$ Ω·m can be modified including stainless steel, gold, aluminum, silicon microstructures, carbon nanotubes, etc.

Figure 3:
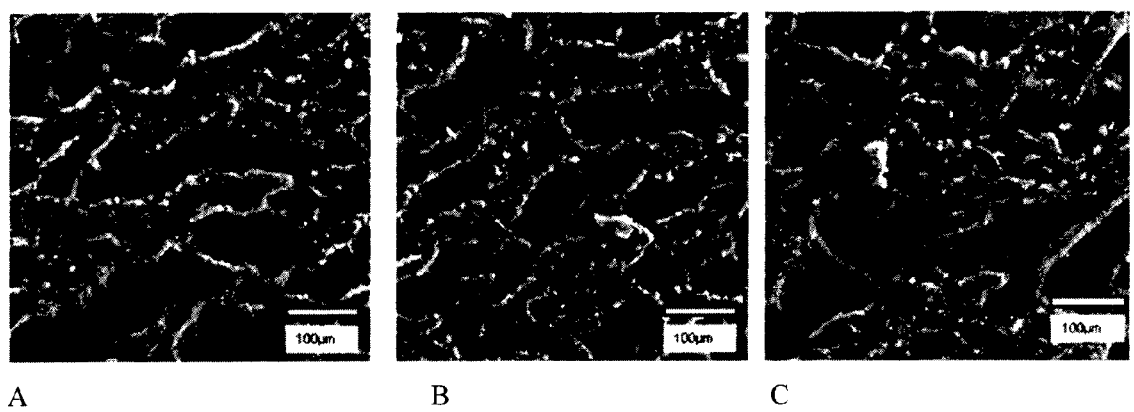

Modification was visible by eye and its microstructure was demonstrated by scanning electron microscopy (FIG. 3).

There were two major advantages of the disclosed approach. At first, the modification was performed at ambient conditions. Secondly, elevated temperature needed for partial solvent removal was accomplished by a simple device. Instead of cold particles hot droplets effectively arrived at the surface as a focused beam by application of high external electric field. The particles carried opposite charge than the surface as well as the mask positioned at a distance <3 mm from the surface. Mechanically stable deposit of titanium, zirconium or hafnium oxides represented a spongy micro porous structure, which was rugged and useful for efficient phosphopeptide preconcentration.

The instrument depicted in FIG. 1 was used for the surface modification consisting of an electrospraying part, heated compartment and surface to be modified terminal part. The electrospray part involved a T-shaped piece mounted on a syringe pump. The pump pressurized the piston of a syringe containing an alkoxide stock solution (0.001-0.5 mol·$L^{-1}$). The solution was pumped through Teflon tubing into a T-piece at a 5-10 µL/min flow rate. The T-junction was terminated by a spray needle. The T-piece was also supplied with pressurized carrier gas valve inlet operated at 0.2-0.8 MPa. Further, the instrument consisted of a high voltage (1000-8000 V) power supply conductively linked with the metallic part of the syringe. Externally heated compartment was held at 50-350° C. The terminal part contains the surface to be modified. It can contain the mask which either is grounded or linked with a second high-voltage power supply (up to ±8000V). If mask is not in place, the high voltage can be applied directly to the surface for modification. The mask distance is less than 15 mm from the heated compartment and less than 3 mm from the surface for modification. The distance between surface and heated compartment outlet can be reduced to less than 20 mm if mask is not in place.

The surface modification process can be described in the following way: electric power supply was linked to electrospray part. Alkoxide solution A was sampled to a stream of pressurized carrier gas. In the presence of high voltage and a stream of pressurized gas the alkoxide solution A was electronebulized from the spray needle to form a charged aerosol B. The nebulized aerosol was focused to heated compartment for final drying.

Hyperthermal aerosol formed this way was changed to a dry aerosol or a cloud of charged particles C. Dried charged particles C can be focused to the surface for modification by high electric field applied to the mask or the surface, which is of opposite polarity than voltage applied to electrospray. The high internal energy content obtained from fast particle heating can be used for efficient macroscopic and homogeneous particle imprint on the surface. The shape and size of this imprint was defined by shape and size of mask slots. If mask was not in place, then the imprinted dimensions were defined by the outlet diameter of the heated compartment. The modified surface functionalized this way can be used for phosphopeptide preconcentration and upon addition of ionization matrix the enriched phosphopeptides can be analyzed by any desorption/ionization mass spectrometry technique (e.g. MALDI). Modified surface was illustrated by electron microscopy scan and depicted in FIG. 3.

The described way of surface modification provided high quality rigid and stable layers that were breach free and homogeneous.

The analyses of phosphopeptides originated from casein standard tryptic digestion were illustrated in Examples 1-3. The acquired data were compared to those reported in literature. Twenty phosphopeptides were identified by the application of modified surfaces disclosed in this invention. On the contrary, just two to eight phosphopeptides originated from casein tryptic digests were reported from literature (FIGS. 5 and 6). Hence, much better analytical results were achieved when modified surfaces disclosed in this patent application were used.

FIGURES

FIG. 1

Apparatus dedicated for the preparation of modified surfaces to be utilized by desorption/ionization mass spectrometry consists of a T-piece 1, syringe pump 2 pressurizing the piston 3 of a syringe 4 containing the stock solution A, tubing 5, spray needle 6, carrier gas inlet 7, high-voltage source 8 applying high electric voltage to a conductive part 9 of a syringe 4, heated compartment 10, high-voltage source 11, surface 12 for modification and mask 13. Spraying the stock solution gives rise to charged aerosol B which in turn is converted to dry aerosol/gas C by passing the heated compartment.

FIG. 2

Apparatus dedicated for the preparation of modified surfaces to be utilized by desorption/ionization mass spectrometry consists of a T-piece 1, syringe pump 2 pressurizing the piston 3 of a syringe 4 containing the stock solution A, tubing 5, spray needle 6, carrier gas inlet 7, high-voltage source 8 applying high electric voltage to a conductive part 9 of a syringe, heated compartment 10, high-voltage source 11, surface 12 for modification. Spraying the stock solution gives rise to charged aerosol B which in turn is converted to dry aerosol/gas C by passing the heated compartment.

FIG. 3

Electron microscopy scans of modified surfaces: A) surface modified according to example 1, B) surface obtained according to example 2, C) surface obtained according to example 3. Electron microscopy images reveal high-quality surfaces by spongy oxide layer. The surface is breach free and homogeneous.

FIG. 4

Comparison of results of identical sample analysis containing tryptic peptides obtained from a surface according to this invention and from a non-modified surface. Identified phosphopeptides are labeled by arrows. A) MALDI mass spectrum of casein tryptic peptides obtained from a standard surface. B) MALDI mass spectrum of casein peptides obtained from a modified surface according to the example 1. C) MALDI mass spectrum of casein peptides obtained from a modified surface according to the example 2. D) MALDI mass spectrum of casein peptides obtained from a modified surface according to the example 3.

FIG. 5

Figure 4:
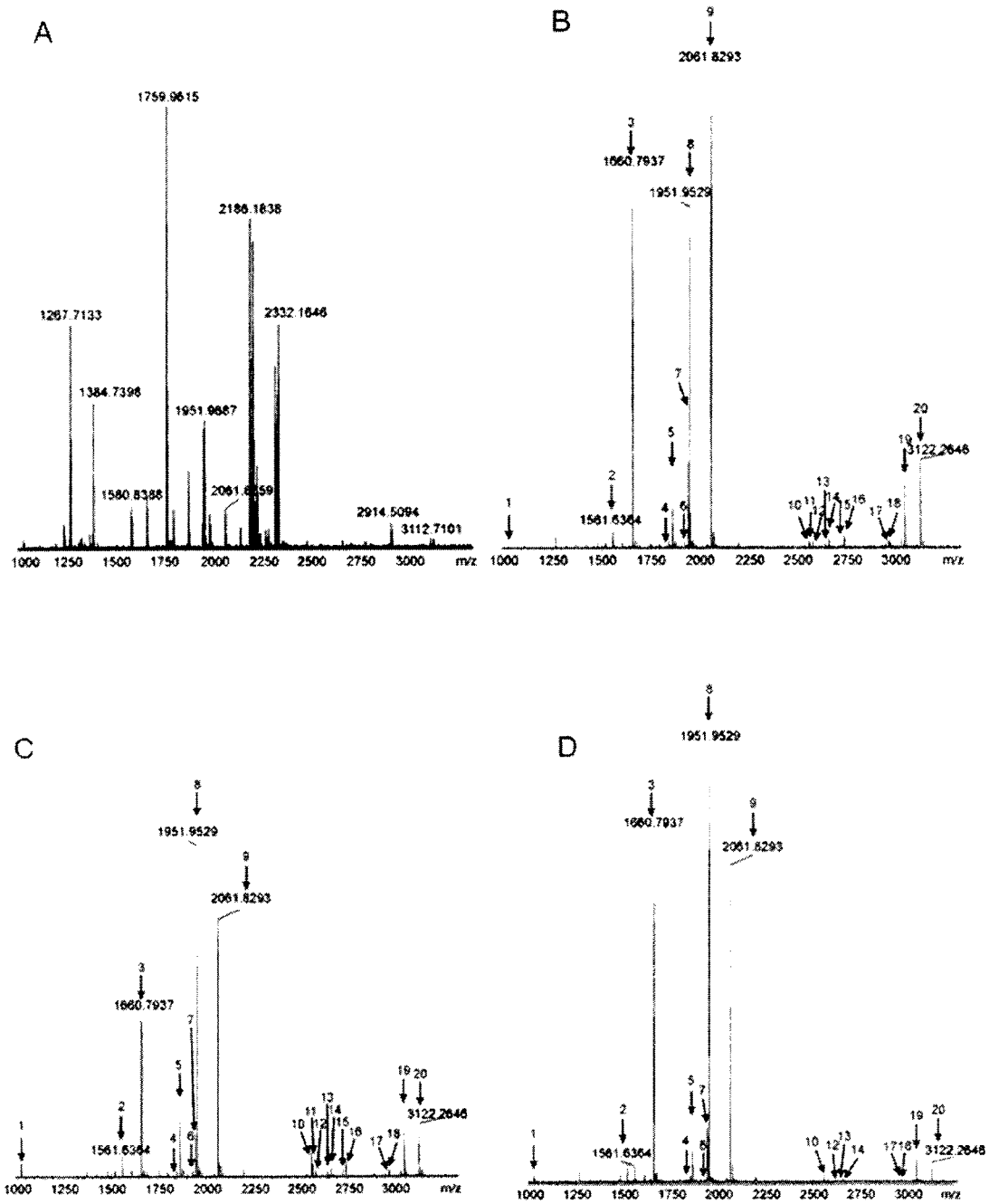

Comparison of data on beta casein obtained according to this invention with those from literature. First column defines the peak number in mass spectrum depicted in FIG. 4B, in which the surface was prepared according to Example 1. Second column defines the m/z ratio of detected ions (the corresponding charge is shown in parentheses). The third column declares the peptide sequence including the phosphorylation site location. The number of phosphorylated sites and casein subunit definition are depicted in 4th and 5th column, respectively. Sixth to tenth column report the literature data:
2=Eriksson A., et al., Anal. Chem. 2010, 82, 4577-4583
3=Bi H., et al., Anal. Chem. 2009, 81, 1177-1183
4=Torta F. et al., Journal of Proteome research, 2009, vol. 8, No. 4, 1932-1942

5=Larsen R. M. et al., Molecular & Cellular Proteomics, 2005
6=Hoang T. et al., Anal. Chem. 2010, 82, 219-228
Flags "+" and "−" define the phosphopeptide presence or absence, respectively.

FIG. 6

Comparison of data on alpha S1 casein obtained according to this patent application with those from literature. First column defines the peak number in mass spectrum depicted in FIG. 4B. Second column defines the m/z ratio of detected ions (the corresponding charge is shown in parentheses). The third column declares the peptide sequence including the phosphorylation site location. The number of phosphorylated sites and casein subunit definition are depicted in 4th and 5$^{th}$ column, respectively. Sixth to tenth column report the literature data:
1=Blacken R. G. et al., Anal. Chem. 2007, 79, 5449-5456
2=Eriksson A., et al., Anal. Chem. 2010, 82, 4577-4583
4=Torta F. et al., Journal of Proteome research, 2009, vol. 8, No. 4, 1932-1942
5=Larsen R. M. et al., Molecular & Cellular Proteomics, 2005
6=Hoang T. et al., Anal. Chem. 2010, 82, 219-228
Flags "+" and "−" define the phosphopeptide presence or absence, respectively.

EXAMPLES

Example 1

The modified surface was prepared via dry electrospray deposition in 15 minutes according to the following workflow:
Apparatus (FIG. 1) variables were adjusted accordingly:
Flow rate of Syringe pump 2: 5 µL/min
Voltage from high-voltage source 8 applied to conductive part 9 of the syringe 4: 3500 V
Temperature of heated compartment 10 in tubular form: 130° C.
Voltage from source 11 applied to mask 13: −5 000 V
Carrier gas pressure in inlet 7: 0.5 MPa
Carrier gas: nitrogen
Orifice shape in mask: circle with 1 mm diameter The syringe pump 2 was filled with a solution of zirconium propoxide in 2-propanol (0.02 mol/l (solution A). High-voltage source 8 was connected to a conductive part 9 of a syringe 4 containing the stock solution. Syringe 4 was connected to the T-piece 1 via tubing 5. Alkoxide solution A was sampled to the T-piece 1 using a syringe pump 2 and by application of high voltage and carrier gas it was electronebulized from the spray needle to form the charged aerosol B. The created aerosol passed through the heated compartment 10 represented by a tubing of 5 mm diameter and mask 13 to land at the stainless steel surface 12. Upon terminating the procedure the high-voltage sources 8 and 11 were switched off eliminating the electric potentials previously applied to electrospray and mask. Then the modified surface was removed, washed with 2-propanol, ethanol and water. During the procedure 1.5 µmol zirconium propoxide was consumed and the spot of a modified surface had circular profile with 1 mm diameter (defined by mask). The layer was sufficiently stable both for sample preparation and for consequent peptide analysis.

Example 2

The modified surface was prepared via dry electrospray deposition in 15 minutes according to the following workflow:
Apparatus (FIG. 1) variables were adjusted accordingly:
Flow rate of syringe pump 2: 8 µL/min
Voltage from high-voltage source 8 applied to conductive part 9 of the syringe 4: −3000 V
Temperature of heated compartment 10 in tubular form: 100° C.
Voltage from high-voltage source 11 connected to mask 13: +6000 V
Carrier gas pressure in inlet 7: 0.4 MPa
Carrier gas: argon
Orifice shape in mask: circle with 0.5 mm diameter The syringe pump 2 was filled with a solution of zirconium propoxide in 1-propanol (0.03 mol/l (solution A). High-voltage source 8 was connected to a conductive part 9 of a syringe 4 containing the stock solution. Syringe 4 was connected to the T-piece 1 via tubing 5. Alkoxide solution A was sampled to the T-piece 1 using a syringe pump 2 and by application of high voltage and carrier gas it was electronebulized from the spray needle to form the charged aerosol B. The created aerosol passed through the heated compartment 10 represented by a tubing of 5 mm diameter and mask 13 to land at the glass surface 12 for modification. Upon terminating the procedure the high voltage sources 8 and 11 were switched off eliminating the electric potentials previously applied to electrospray and mask. Then the modified surface was removed, washed with 2-propanol, ethanol and water. During the procedure 3.6 µmol zirconium propoxide was consumed and the spot of zirconium oxide had circular profile with 0.5 mm diameter (defined by mask). The layer was sufficiently stable both for sample preparation and for consequent peptide analysis.

Example 3

Figure 2:
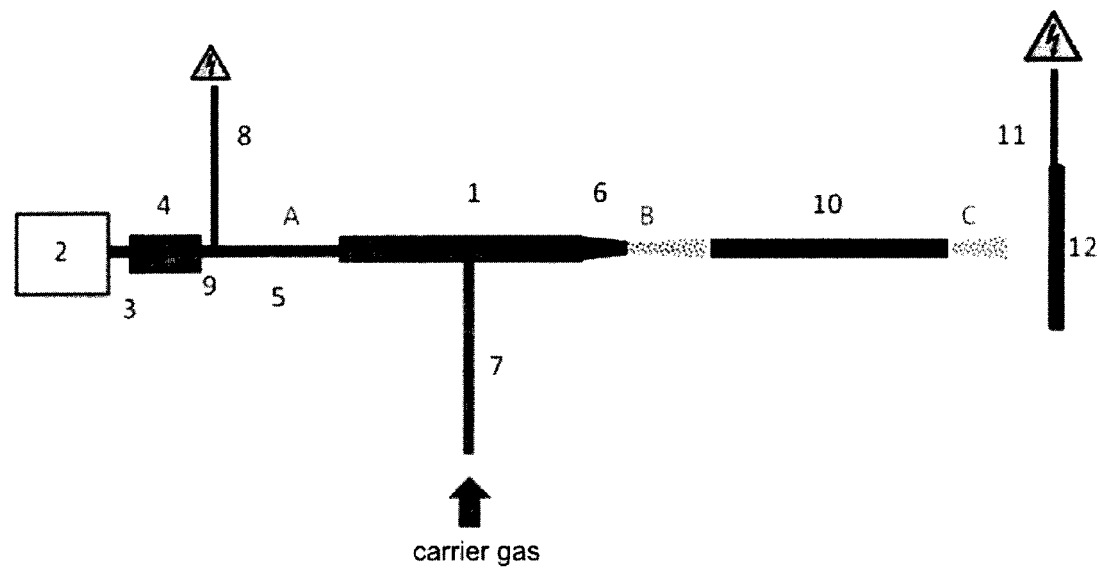

The modified surface was prepared via dry electrospray deposition in 20 minutes according to the following workflow:
Apparatus (FIG. 2) variables were adjusted accordingly:
Flow rate of syringe pump 2: 6 µL/min
Voltage from high-voltage source 8 applied to conductive part 9 of the syringe 4: +3000 V
Temperature of heated compartment 10 in tubular form: 120° C.
Voltage from high-voltage source 11 connected to surface 12 for modification: +6000 V
Carrier gas pressure in inlet (7): 0.5 MPa
Carrier gas: carbon dioxide The syringe pump 2 was filled with a solution of titanium propoxide in 1-butanol (0.05 mol/l (solution A). High-voltage source 8 was connected to a conductive part 9 of a syringe 4 containing the stock solution. Alkoxide solution A was sampled to the T-piece 1 using a syringe pump 2 and by application of high voltage and carrier gas it was electronebulized from the spray needle to form charged aerosol B. The created aerosol passed through the heated compartment 10 represented by a tubing of 5 mm diameter and mask 13 to land at the aluminum surface 12. Upon terminating the procedure the high voltage sources 8 and 11 were switched off. Then the modified surface was removed, washed with 2-propanol, ethanol and water. During the procedure 6 µmol titanium propoxide was consumed and the spot of titanium oxide had circular profile with 5 mm diameter (defined by outlet diameter of the heated compartment). The layer was sufficiently stable both for sample preparation and for consequent peptide analysis.

Example 4

The preparation of phosphopeptide mixtures from casein and their enrichment on modified surfaces according to examples 1, 2 and 3.
Casein (10 µg, Sigma-Aldrich) was separated using SDS-PAGE on a commercial gradient gel (Invitrogen). After the separation the gel was stained using CBB-R250 and the gel part with visualized protein spot was cut out and sliced to small cubic blocks (~1 $mm^3$). The protein was de-stained, reduced (50 mM TCEP, pH 8), alkylated (55 mM iodoacetamide, pH 8) and digested with trypsin. The resulting peptides and phosphopeptides were extracted from gel, desalted on reversed phase material (microtrap, Michrom), dried and subsequently used for performance evaluation of the modified surface as a standard test mixture. The surface was thrice washed by methanol and five times with DHB buffer. Casein tryptic peptide mixture was dissolved in 40 μL DHB buffer (20 mg/mL dihydroxybenzoic acid in acetonitrile/water/trifluoroacetic acid=50:49.9:0.1 (v/v)). The obtained sample solution (0.7 μL) was loaded on a surface at room temperature and let to dry. The dry spot was washed five times with DHB buffer and then dipped for three minutes into acetonitrile/water/trifluoroacetic acid=80:19.9:0.1 (v/v) solution for non-phosphorylated peptide removal. Then 0.5 μL ammonia solution (400 mM) was added and let to complete dryness. Another 0.5 μL of trifluoroacetic acid (2%) was subsequently added and again let to dry. Finally, the ionization matrix solution (acetonitrile/water/phosphoric acid=50:49:1, v/v) placed on surface and analyzed by standard MALDI approach. The resulting mass spectrum was depicted in FIG. 4B.

Data Collection and Their Examination on the Presence of Phosphopeptides

FIG. 3, panel A, illustrated the MALDI mass spectrum of tryptic peptides derived from casein obtained by standard approaches utilizing non-modified surfaces. Panels B, C, and D demonstrated enriched phosphopeptide mixtures obtained by using examples 1, 2, and 3, respectively. Spectral comparison showed the enhanced signals at m/z 1031, 1562, 1661, 1833, 1864, 1928, 1944, 1952, 2062, 2556, 2560, 2577, 2640, 2657, 2720, 2737, 2966, 2962, 3042, 3122 (see FIGS. 5 and 6) in Panel B (modified surface) contrary to Panel A (standard surface). These enhanced signals were attributed to phosphopeptides being enriched due to the surface modification process.

INDUSTRIAL APPLICABILITY

Instrumental biological analysis of proteins, particularly phosphoproteomics

The invention claimed is:

1. A method of a surface modification for analyzing of phosphorylated peptides characterized in that an alcoholic solution of zirconium/titanium/hafnium alkoxide (A) and a pressurized carrier gas of about 0.2 to 0.8 MPa are transferred to a closed compartment of a T-piece (1), the closed compartment of the T-piece (1) is kept under voltage of ±800 to 8000 V, and it contains an electrospray needle (6), from which a created nebulized aerosol (B) is sprayed, and the created nebulized aerosol (B) is transferred through a heated compartment (10), that is held under 50 to 250° C., from which dried particles (C) are brought out, and the dried particles (C) are focused to a surface (12) for modification.

2. The method of surface modification according to claim 1 characterized in that surface (12) for modification is conductive with a maximal resistivity of $10^{20}$ Ω·m and is kept under voltage of ±500-10000 V and is of an opposite polarity than the T-piece (1).

3. The method of surface modification according to claim 1 characterized in that a mask (13) is placed between the surface (12) for modification and the heated compartment (10) at a distance less than 3 mm from the surface (12) for modification, and the mask (13) is kept under voltage of ±500-10000 V of an opposite polarity than the T-piece (1).

4. The method of surface modification according to claim 1 characterized in that the pressurized carrier gas is nitrous oxide or molecular nitrogen or carbon dioxide, or neon, or argon, or krypton, or xenon, or radon, or oxygen.

5. The method of surface modification according to claim 1 characterized in that the surface (12) for modification is made from glass, or silicon nanostructures, or carbon nanotubes or metal or its composite thermally stable metal to 250° C. or synthetic polymer or its composite thermally and mechanically stable to 250° C.

* * * * *